United States Patent
Edmonson et al.

(10) Patent No.: US 7,383,072 B2
(45) Date of Patent: Jun. 3, 2008

(54) SWEAT SENSOR SYSTEM AND METHOD OF CHARACTERIZING THE COMPOSITIONAL ANALYSIS OF SWEAT FLUID

(75) Inventors: Peter J. Edmonson, Hamilton (CA); Douglas W. Stoddard, Toronto (CA)

(73) Assignee: P. J. Edmonson Ltd, Hamilton, Ontario (CA)

( * ) Notice: Subject to any disclaimer, the term of this patent is extended or adjusted under 35 U.S.C. 154(b) by 397 days.

(21) Appl. No.: 11/124,045

(22) Filed: May 9, 2005

(65) Prior Publication Data

US 2006/0253011 A1 Nov. 9, 2006

(51) Int. Cl.
*A61B 5/05* (2006.01)
*A61B 5/00* (2006.01)

(52) U.S. Cl. ............ 600/346; 600/345; 600/348; 600/362

(58) Field of Classification Search .......... 600/346, 600/362, 348
See application file for complete search history.

(56) References Cited

U.S. PATENT DOCUMENTS

| | | | |
|---|---|---|---|
| 5,050,604 A * | 9/1991 | Reshef et al. | 600/346 |
| 6,198,953 B1 | 3/2001 | Webster et al. | |
| 2003/0028089 A1 * | 2/2003 | Galley et al. | 600/365 |
| 2003/0028122 A1 * | 2/2003 | Marett | 600/551 |
| 2004/0115754 A1 * | 6/2004 | Chang | 435/14 |
| 2004/0193030 A1 * | 9/2004 | Aston et al. | 600/362 |

* cited by examiner

*Primary Examiner*—Robert L. Nasser, Jr.
*Assistant Examiner*—Patricia Mallari
(74) *Attorney, Agent, or Firm*—Robert F. Delbridge

(57) ABSTRACT

A method of sensing the concentration level of at least one particular electrolyte in the sweat fluid of a subject, includes providing a sweat sensor system having sweat fluid absorbing material, measuring apparatus for sensing the electrical conductivity of sweat fluid absorbed by the absorbing material and producing ionic concentration data for said at least one particular electrolyte, and a user interface connected to the measurement apparatus for interpreting the data to a user. The absorbing material is applied to the skin of the subject to cause sweat fluid thereon to be absorbed by the absorbing material whereby the measurement apparatus produces ionic concentration data for the sweat fluid absorbed and the user interface interprets the data for a user.

14 Claims, 9 Drawing Sheets

SWEAT SENSOR SYSTEM AND METHOD OF CHARACTERIZING THE COMPOSITIONAL ANALYSIS OF SWEAT FLUID

FIELD OF INVENTION

This invention relates to sweat sensor systems for sensing the rate of sweat fluid lost and the concentration levels of particular electrolytes in sweat fluid and to methods of characterizing the compositional analysis of sweat fluid of a subject.

BACKGROUND OF INVENTION

It is often advantageous to monitor and carry out an analysis of both the rate of production and the composition of a person's sweat while they are performing strenuous physical exertion, since such knowledge enables the individual to more accurately replenish lost sweat fluid and electrolytes. The analysis of sweat may also be useful for other reasons, such as diagnosing cystic fibrosis, since such analysis currently forms the basis on which such a diagnosis is made.

SUMMARY OF INVENTION

According to one aspect of the invention, a method of characterizing the compositional analysis of sweat fluid of a subject involves use of an embedded algorithm in measuring apparatus which, when provided with the ionic concentrations of predetermined electrolytes, advises the user through a user interface what would be the required amount and composition of electrolyte containing liquid to be taken to achieve the proper balance of electrolytes during sweat loss.

In accordance with another aspect of the invention, a sensor device is placed on or near the skin of a person, the sensor device being associated with measurement apparatus which determines the compositional analysis of sweat by sensing the electrical conductivity of sweat fluid.

Sweat fluid contains an electrolyte concentration which includes amounts of sodium, potassium, calcium, magnesium and other substances. The ionic variation within the sweat fluid during various degrees of physical exertion or due to certain conditions such as cystic fibrosis varies the conductivity of the fluid. One method of measuring such variation in conductivity is to use a simple direct current (DC) conductivity measurement between two electrodes placed in contact with the sweat fluid. The sweat fluid acts as a DC electrical path between the two electrodes with a varying conductivity depending on the electrolyte composition.

It is also possible to measure the conductivity of sweat fluid by means of electrochemical microsensors which measure resistance or current through an analyte. Such electrochemical microsensors may be Surface Acoustic Wave (SAW) sensors and identification devices which are passive radio frequency (RF) devices capable of exchanging information over both wired and wireless media. Such SAW devices may be configured with selectable reflector arrays whose reflective characteristics vary with variation of a conductive load attached to the reflector arrays. As a SAW sensor device is interrogated by an RF signal, the reflected signal will contain a data stream similar to the data selected within each reflective segment of the reflector array and is returned to the interrogator.

A SAW sensor or identification device may have a fluidic channel through which sweat fluid can flow to pass over split finger electrodes. This enables metallized split finger electrodes to behave as electrochemical microsensors. The conductivity of the sweat fluid effectively controls the load of the reflector segment, thereby producing a magnitude and phase response characteristic of the compositional analysis of the sweat.

A major advantage of the use of SAW sensors and identification devices is the ability to remotely monitor a person via a wireless interface. This permits the monitoring of multiple individuals within an athletic field of play, a battle field or other area where individuals are attempting to perform at their maximum performance under strenuous conditions. Such monitoring may be as taught in U.S. patent application Ser. No. 10/729,920 filed Dec. 9, 2003 in the names of Peter J. Edmonson and Colin K. Campbell and entitled "Selectable Reflector Arrays for SAW Sensors and Identification Devices".

As previously indicated, there are many scenarios where the monitoring of the composition of sweat of individuals while undergoing demanding physical exertion is beneficial. Generally, people ingest fluids during such exertion to replace fluids lost through sweating but they have no real feedback system to correctly identify the amount or type of electrolyte supplements to consume along with the proper amount of fluids. The present invention enables individuals to characterize their sweat fluid loss and their sweat composition and then take suitable action to react to the analysis.

A sweat monitoring device locatable on or near an individual's skin would be ideal for all people who are concerned about the compositional analysis of their sweat. An individual participating in strenuous sports, exercise or work activities would be able to monitor their sweat fluid loss and composition by wearing a portable monitor. Such a monitor would obtain sweat data, analyse the data and then display the outcome of the analysis. Individuals participating in a team effort would have the option of wearing an individual self-contained sweat monitoring device or a wireless sweat sensor which would obtain the sweat data and then wirelessly send the data to a central transceiver where the data analysis and display would be located. This would enable individuals to wear small sensors which would not impede their activities, and also enable them to congregate around a central point equipped with a sweat sensor transceiver, such as an athletic team bench, work station or work vehicle.

The invention can benefit individuals in the assessment of their sweat composition, thereby enabling them to more accurately replenish lost sweat electrolyte. This would reduce the chances of developing various electrolyte balance disorders, including hyponatremia and hypokalemia. Individuals may suffer from hyponatremia and hypokalemia during exercise by underreplacing sodium or potassium respectively relative to the levels lost through sweating. Another benefit is the clinical diagnosing of cystic fibrosis by sensing the electrical conductivity of the sweat, as reported by K. B. Hammond et al, "Clinical evaluation of the macroduct sweat collection system and conductivity analyzer in the diagnosis of cystic fibrosis," The Journal of Pediatrics, February 1994. The sensor would obtain sweat data, analyse the data and then display the value of the electrolyte components.

In accordance with a particular aspect of the invention, a sweat sensor system for sensing the concentration levels of particular electrolytes in sweat fluid has a first absorbing material positionable in contact with sweat fluid, a larger portion of absorbing material positionable in contact with the first absorbing material but not in contact with the sweat fluid, a pair of spaced electrodes in contact with the first absorbing material and located between the sweat fluid and the larger portion of absorbing material, measuring apparatus connected to the electrodes to produce ionic concentration data, and a user interface connected to the measurement apparatus for interpreting the data for a user.

In accordance with another particular aspect of the invention, a method of characterizing the compositional analysis of sweat fluid of a subject includes periodically measuring the electrical resistance of the sweat fluid and thereby determining the temporal ionic concentrations of predetermined electrolytes, determining from previous collected data whether the subject has time-based normal or non-normal ionic concentration levels, and recommending to the subject any required action to be taken.

It should also be noted that a sweat monitor in accordance with the invention could also house a heart rate sensor, clock, stopwatch and other functions which would assist an individual to supervise their activity. A sweat monitor in accordance with the invention could be programmed to store data parameters of several users so that when each of the users activates the system, their previous accumulated data parameters are recalled.

DESCRIPTION OF THE DRAWINGS

Embodiments of the invention will now be described, by way of example, with reference to the accompanying drawings, of which.

DESCRIPTION OF PREFERRED EMBODIMENTS

Figure 1:
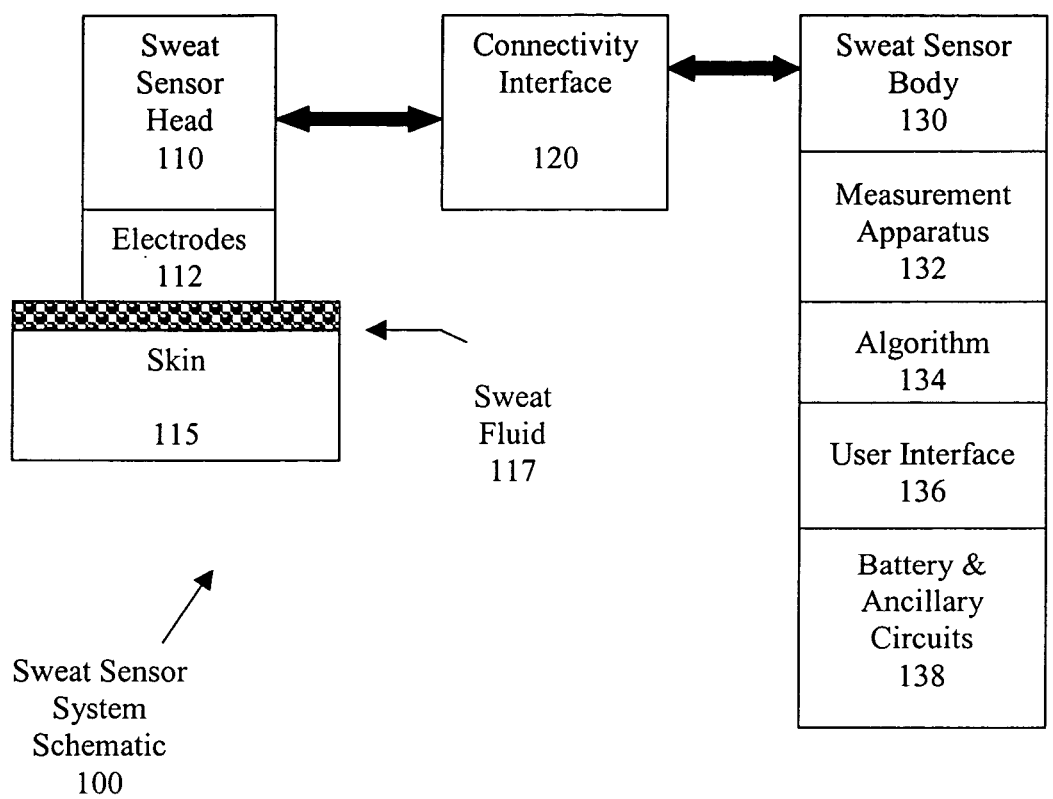
FIG. 1 is a schematic diagram of a sweat sensor system including a sensor head, connectivity interface and sweat sensor body.

Referring to the drawings, a sweat sensor system which characterizes the compositional analysis of sweat is illustrated in an overall system schematic diagram 100 shown in FIG. 1. A sweat sensor head 110 is positionable on or in close proximity to the skin 115 of a person to determine the compositional ionic content of their sweat fluid 117. The sweat sensor head 110 absorbs samples of the sweat fluid 117 and, with the use of two electrodes 112, presents a measurable parameter to a connectivity interface 120. The connectivity interface 120 also links with a sweat sensor body 130.

A measurement apparatus 132 contained within the sweat sensor body 130 suitably processes the measurable parameter received from two electrodes 112 via the connectivity interface 120. An algorithm 134 contained within the sweat sensor body 130 determines the outcome of the measurable parameter and suitably presents the data to a user interface 136. Other components such as a battery and other ancillary circuits 138 make the sweat sensor system self-reliant and appropriate for portable use.

Figure 2:
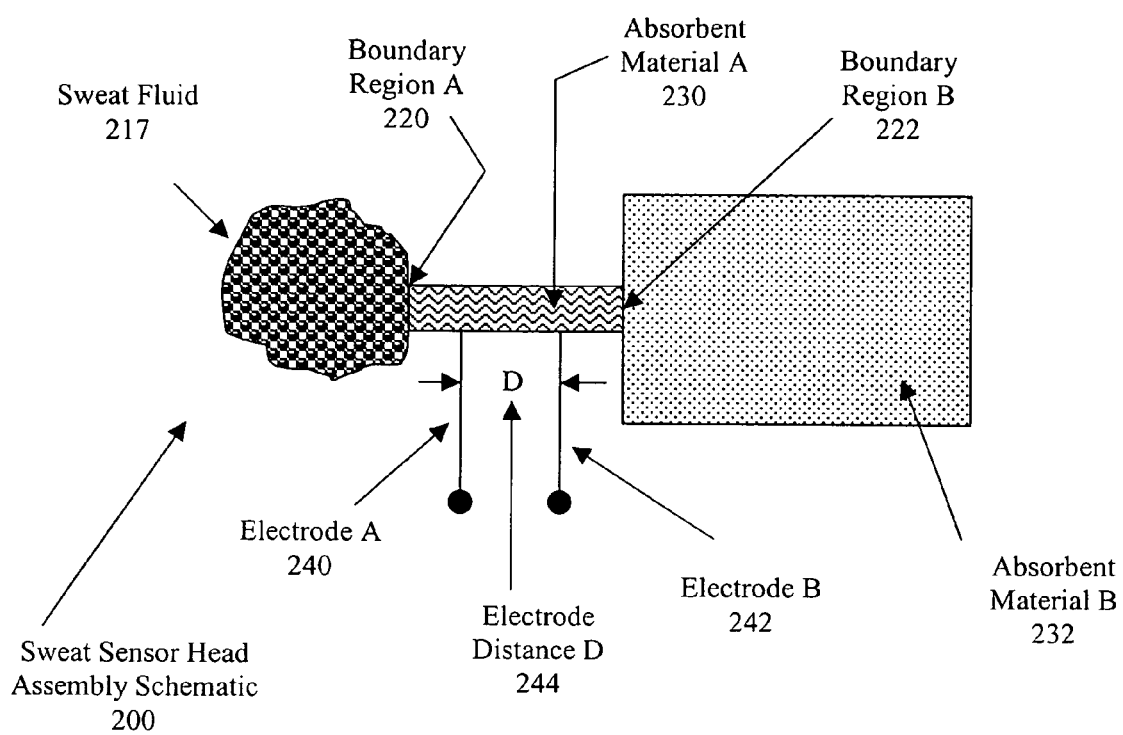
FIG. 2 is a schematic diagram of the sensor head illustrating the passive pumping system.

The purpose of the sweat sensor head 110 shown in FIG. 1 is to sample sweat fluid from the surface of a subject's skin and present this fluid to a pair of electrodes 112. A schematic diagram of the fundamental assembly of the sweat sensor head 200 is shown in FIG. 2. It is necessary to prevent any electrolysis action between the two electrodes. If the sweat fluid is in a static state such that the two electrodes are in contact with the sweat fluid, there will then be a tendency for sodium ($Na^+$) ions to move towards the cathode electrode. The area surrounding the cathode then begins to accumulate certain ions which form a barrier to the sweat fluid. It has been found that agitation temporarily removes this ionic barrier but, as conditions settle to a static state, the barrier forms again.

The sweat sensor head 200 substantially eliminates such a problem by utilizing an absorbent material A 230 which comes into contact with the sweat fluid 217 at a boundary region A 220. If the density of the sweat fluid 217 is higher on the sweat fluid side of the boundary region A 220 than on the absorbent material A side, then the sweat fluid 217 will cross the boundary region A 220 and flow into the absorbent material A 230. Similarly, if the density of the sweat fluid 217 is higher on the absorbent material A side of the boundary region B 222 than on the absorbent material B side, then the sweat fluid 217 will cross the boundary region B and flow into the absorbent material B 232. This permits the sweat fluid to flow past the electrode A 240 and electrode B 242 in a dynamic state and does not allow an ionic barrier to form in the area surrounding electrode A 240 or electrode B 242.

The distance D 244 between electrode A 240 and electrode B 242 has been determined experimentally to preferably be from about 3 to about 7 mm depending on the cross-sectional area of the absorbent material A 230. An appropriate enclosure (not shown) is provided to contain the sweat sensor head assembly. The fluid input is at boundary region A 220 and the outputs are the electrode A 240 and electrode B 242 connections. This arrangement prevents the two electrodes A, B 240, 242 from coming into contact with the subject's skin. The assembly may be disposable and would be replaced when absorbent material B has become saturated.

Figure 3:
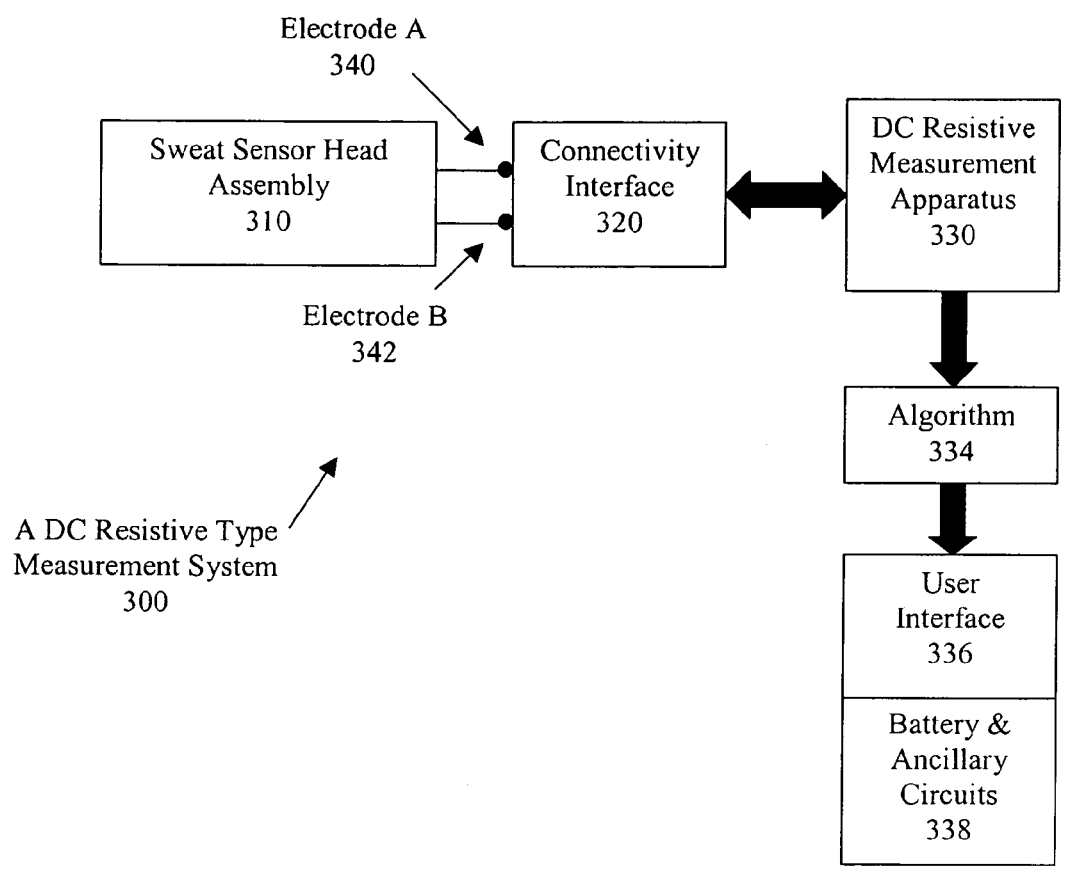
FIG. 3 is a schematic diagram of a resistive type measurement apparatus.

Sweat fluid contains an electrolyte concentration which includes amounts of sodium, potassium, calcium, magnesium and other substances. The ionic variation within the sweat fluid will vary the conductivity or resistance of the liquid. One method of measuring such variation of electrolyte concentration is to use a simple direct current (DC) resistance measurement system 300 as shown in FIG. 3. The sweat head assembly 310 effects contact with the sweat fluid in a manner such that electrode A 340 and electrode B 342 are also in contact with the sweat fluid via an absorbent material, such as absorbent material A 230 of FIG. 2. For this method, the connectivity interface 320 is an electrical connection which is suitably constructed to permit the removable sweat sensor head 300 to be easily disconnected and inserted within the sweat sensor body 130 (see FIG. 1) and yet maintain good electrical connection when inserted. The resistive measurement apparatus 330 may be any of several known types, ranging from a simple ohmmeter to a bridge-style measuring device. The output of the resistive measurement apparatus 330 is conditioned and digitised to produce a binary input format to the algorithm 334. The results of the algorithm are appropriately presented to the user interface 336 with support from the battery and ancillary circuits 338.

Figure 4:
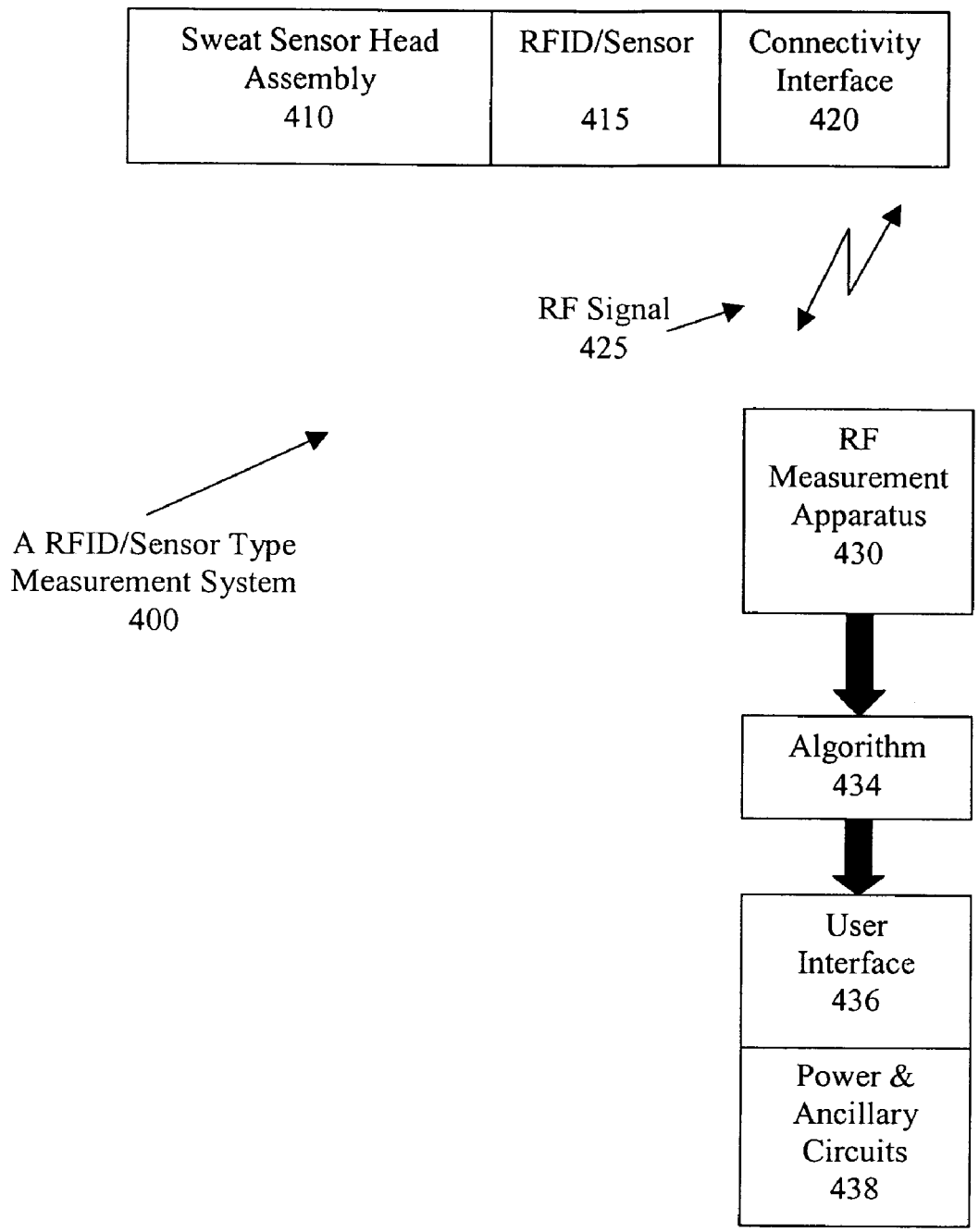
FIG. 4 is a schematic diagram of RFID/sensor type measurement apparatus.

Another method of measuring the variation of electrolyte concentration within a person is to use a remote RFID/sensor measurement system 400 such as illustrated in FIG. 4. A sweat sensor head assembly 410 is housed within the same structure as a RFID/sensor 415 and the connectivity interface 420. For this method, the connectivity interface 420 is in fact a wireless radio frequency (RF) signal 425 between the RFID/sensor 415 and RF measurement apparatus 430. A main advantage of this method is that each individual person need only wear the remote sensor head assembly 410, RFID/sensor 415 and the connectivity interface 420. The RF measurement apparatus 430, along with the remainder of the sweat sensor body 130 containing the algorithm 434, user interface 436 and power and ancillary circuits 438, can be located a suitable distance from the various subjects. This enables a single sensor body 130 with a single RF measurement apparatus 430 to interrogate and measure several individual people, each of whom is wearing a remote sensor head assembly 410, RFID/sensor 415 and connectivity interface 420.

Figure 5:
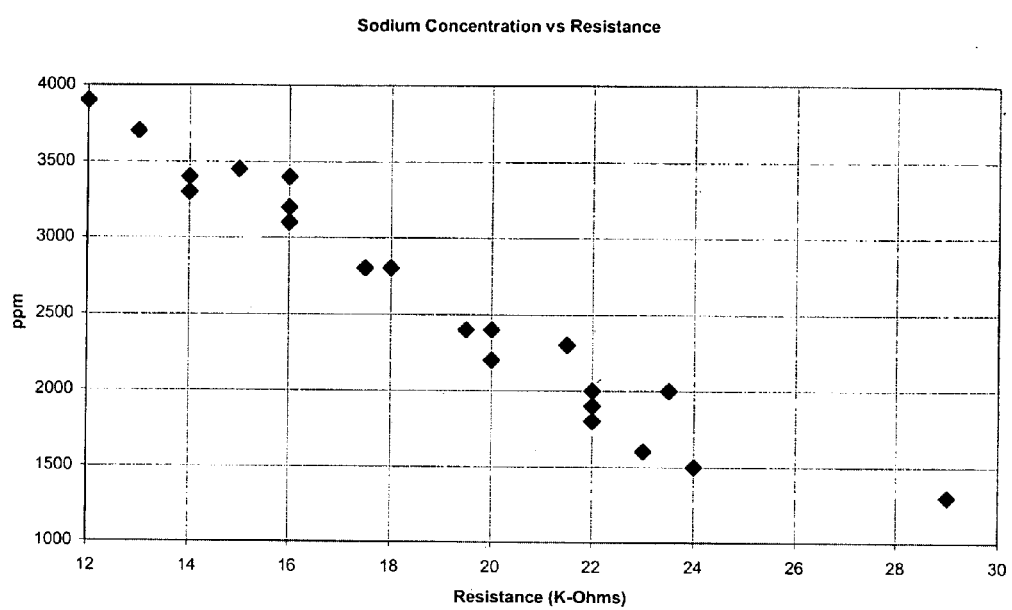
FIG. 5 is a plot of sodium ionic concentration versus resistance.
Figure 6:
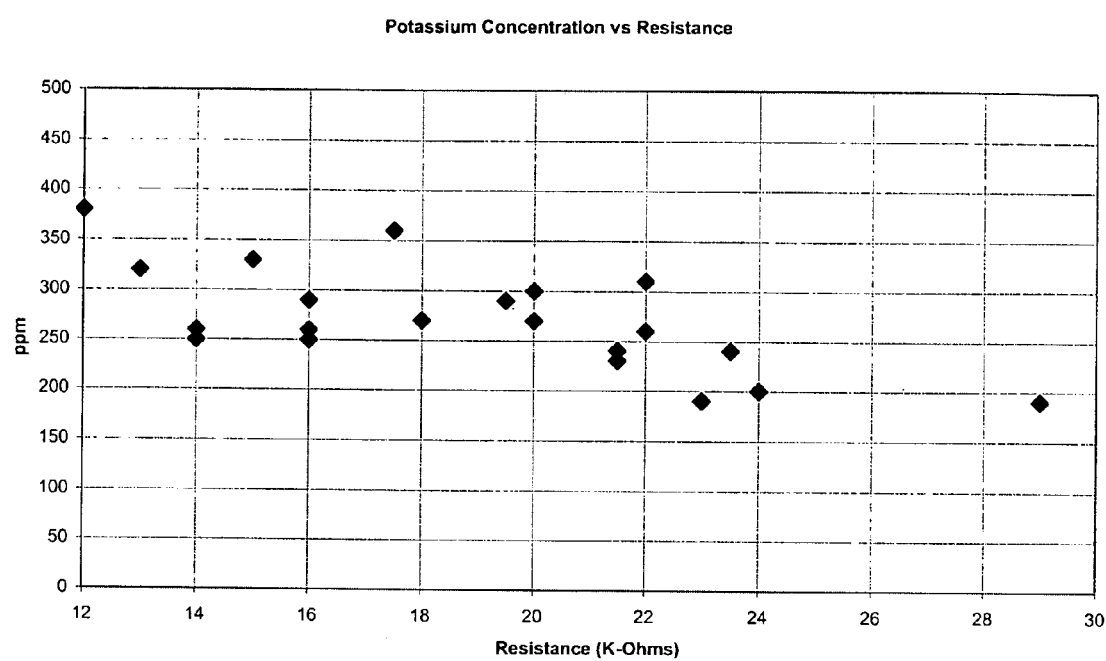
FIG. 6 is a plot of potassium ionic concentration versus resistance.

Sets of experiments were conducted using the sweat sensor system of FIG. 1 and the resistive type measurement apparatus of FIG. 3. Sweat samples were collected from several subjects while they were conducting strenuous physical activities, and each sweat fluid sample was tested for its sodium ionic concentration, potassium ionic concentration and resistance. The ionic meters were manufactured by Horiba, C-131 (potassium) and C-122 (sodium). The ohmmeter was manufactured by Micronta 22-2048. A plot of the sodium concentration in parts-per-million (ppm) versus resistance is shown in FIG. 5. A similar plot of the potassium concentration in ppm versus resistance is shown in FIG. 6. Both plots illustrate the ability to determine the sodium and potassium concentrations of sweat fluid by measuring the resistance of the sweat fluid.

Figure 7:
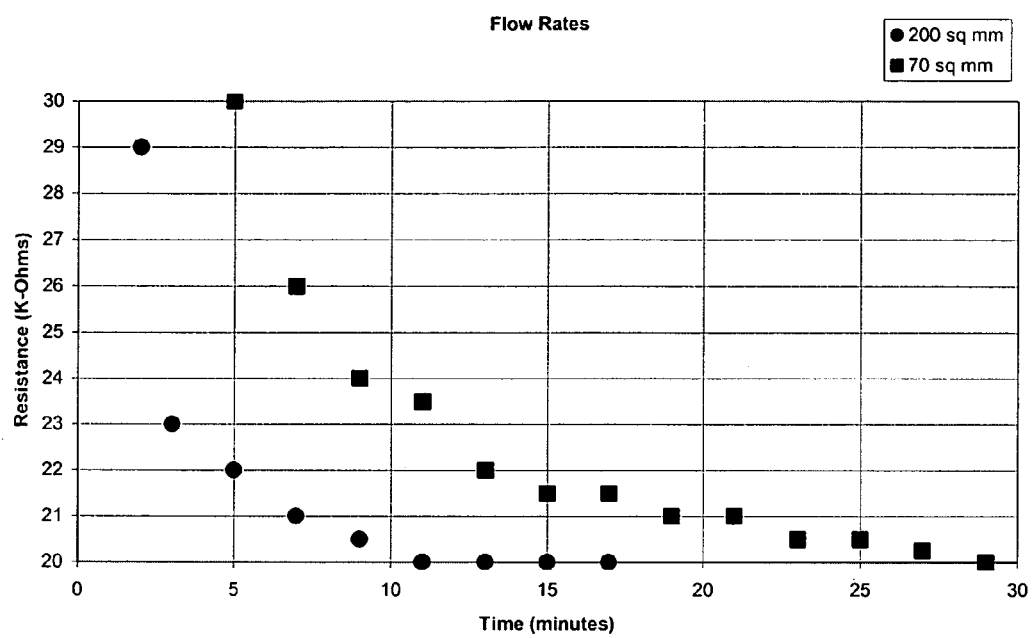
FIG. 7 is a plot of resistance versus time illustrating two different flow rates.

Other sets of experiments were also conducted using the sweat sensor system of FIG. 1, the sweat sensor head assembly of FIG. 2 and the resistive type measurement apparatus of FIG. 3. A small absorbent patch, 200 mm$^2$ in area, was saturated with a sodium solution of 2200 ppm concentration and applied to the boundary region A 220 in two minute intervals. Between each application interval, the absorbent patch was again saturated with the same sodium solution. Similarly, in an other experiment, a smaller absorbent patch, 70 mm$^2$ in area, was saturated with the same sodium solution of 2200 ppm concentration and applied to the boundary region A 220 in two minute intervals. The degrees of saturation of the absorbent material A 230 which the two electrodes A, B 240, 242 reside in will also vary the conductivity or resistance of the liquid. A plot of the rate of change of the resistance versus time is shown in FIG. 7. The time to achieve a steady-state value of 22 K-Ohms, which represents the ionic concentration value of 2200 ppm, correlates with the area of the two patches and the amount of fluid presented to the system.

Figure 8:
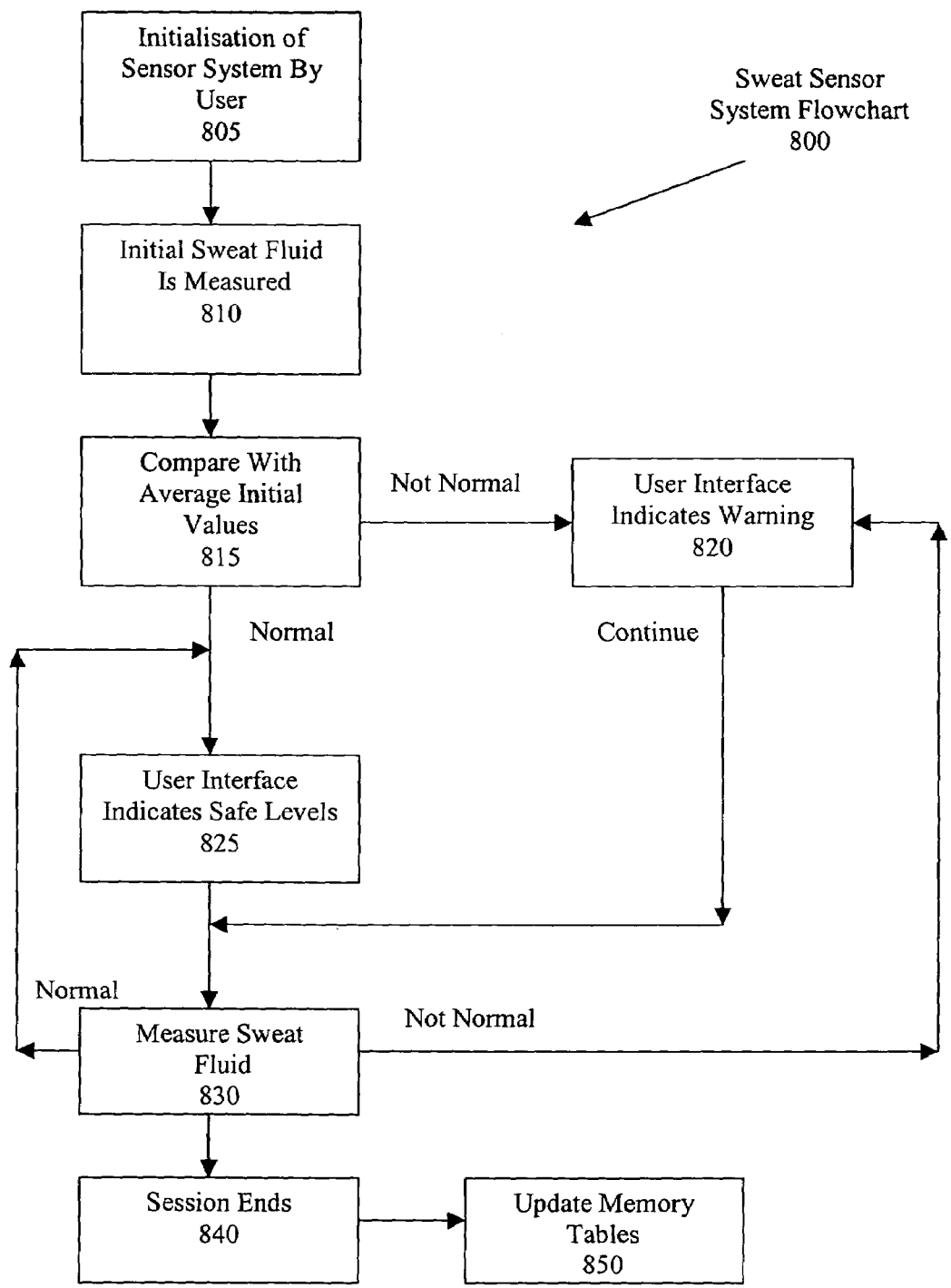
FIG. 8 is a sweat sensor system flow chart for physical activity.

The use of the sweat sensor system shown previously in FIG. 1 is outlined in the system flowchart 800 of FIG. 8. The subject user initially turns on and activates the system via the user interface 805. Ancillary functions such as clock, stopwatch and other monitoring tasks are also activated at this time. Measurement apparatus (such as measurement apparatus 132 of FIG. 1) measures the sweat fluid and determines within the algorithm 134 the ionic concentrations and flow rate of the sweat fluid 810. The algorithm 134 compares the initial value of ionic concentrations with the specific subject and determines from past data logging whether the subject has normal or non-normal ionic concentration levels and flow rates 815. If the ionic concentrations are not normal with respect to the initial data, then a warning 820 is given via the user interface (such as the user interface 136 of FIG. 1). The user interface 136 then recommends the required composition of electrolyte containing liquid to be taken to achieve the proper balance of electrolytes and fluids.

Conversely, if the ionic concentrations and flow rate determined 815 are normal, then the user interface 136 indicates a safe condition 825. Throughout the remainder of the physical strenuous session, the system would continuously perform ionic concentration and flow rate measurements 830 of the subject and continue to indicate, via the user interface 136, the composition of lost sweat, and therefore the recommended composition of replacement electrolyte containing fluid. When the subject ends the physical strenuous session 840, the logged data is updated to memory 850 for further reference by the algorithm 134.

Figure 9:
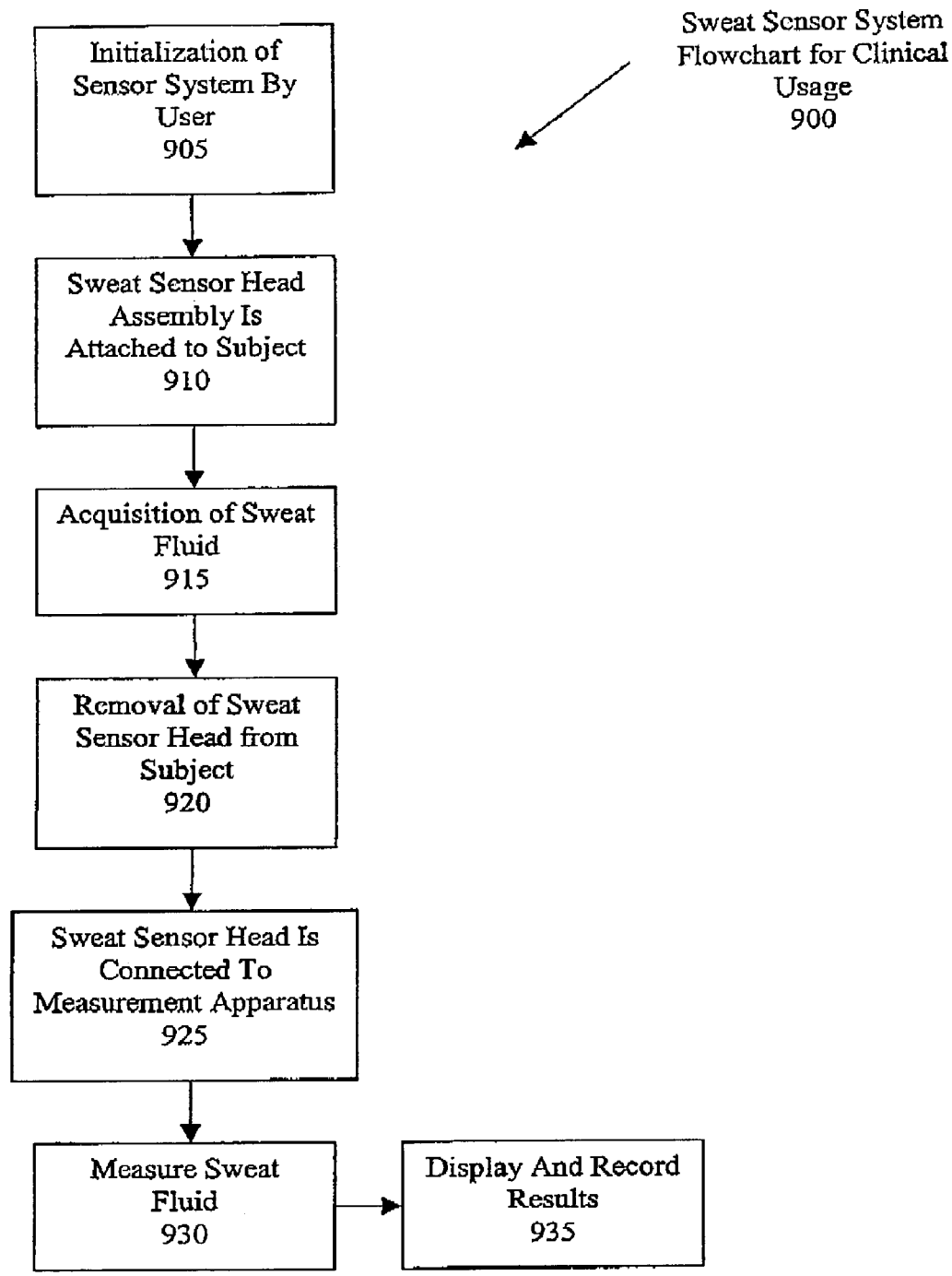
FIG. 9 is a sweat sensor system flow chart for clinical usage.

The clinical use of the sweat sensor system shown previously in FIG. 3 for the diagnosis of cystic fibrosis is shown in the system flowchart 900 of FIG. 9. The subject user initially turns on and activates the system via the user interface 905. The subject has the sweat sensor head assembly 310 attached to their body 910. The sweat sensor head assembly 310 proceeds to collect the subject's sweat fluid 915. After a predetermined time, the sweat sensor head assembly 310 is removed from the subject 920. The sweat sensor head assembly is then connected via the connectivity interface 320 to a measurement apparatus 330, 925. The sweat fluid is then measured 930 and the results are recorded and displayed 935.

The advantages and other embodiments of the invention will now be readily apparent to a person skilled in the art from the foregoing description preferred embodiments, the scope of the inventions being defined in the appended claims.

The invention claimed is:

1. A method of sensing the concentration level of at least one particular electrolyte in the sweat fluid of a subject, the method including:

providing a sweat sensor system having sweat fluid absorbing material, measuring apparatus for sensing the electrical conductivity of sweat fluid absorbed by the absorbing material and producing ionic concentration data for said at least one particular electrolyte, and a user interface connected to the measurement apparatus for interpreting the data to a user, and the measurement apparatus having a pair of spaced electrodes in the sweat fluid absorbing material, the sweat fluid absorbing material comprising a first absorbing material in contact with the sweat fluid, said pair of electrodes being inserted therein, and a larger portion of absorbing material in contact with the first absorbing material but not in contact with the sweat fluid, and applying the absorbing material to the skin of the subject to cause sweat fluid thereon to be absorbed by the absorbing material whereby the measurement apparatus produces ionic concentration data for the sweat fluid absorbed and the user interface interprets the data for the user.

2. A method according to claim 1 wherein the measuring apparatus includes an RFID sensor connected to the user interface.

3. A method according to claim 2 wherein the RFID sensor is connected to the user interface by a wired electrical connection.

4. A method according to claim 2 wherein the RFID sensor is connected to the user interface by an RF connection.

5. A method according to claim 1 wherein the user interface is connected to the measurement apparatus by a wired electrical connection.

6. A method according to claim 1 wherein the user interface is connected to the measurement apparatus by an RF connection.

7. A method according to claim 1 also including determining from previous data of a subject whether the subject has a normal or non-normal ionic concentration level and recommending to the subject any required action to be taken.

8. A sweat sensor system for sensing the concentration level of at least one particular electrolyte in the sweat fluid of a subject, the sensor system including:

sweat fluid absorbing material positionable in contact with sweat fluid on a subject measuring apparatus for sensing the electrical conductivity of sweat fluid absorbed by the absorbing material and producing ionic concentration data for at least one particular electrolyte, and the measuring apparatus including a pair of spaced electrodes in the absorbing material for sensing the electrical conductivity of sweat fluid therein, the sweat fluid absorbing material comprising a first absorbing material positionable in contact with sweat fluid on a subject, said pair of electrodes being inserted therein, and a larger portion of absorbing material positionable in contact with the first absorbing material and not positionable in contact with the sweat fluid, and a user interface connected to the measuring apparatus for interpreting the data to a user.

9. A sweat sensor system according to claim 8 wherein the measuring apparatus includes an RFID sensor connected to the user interface.

10. A sweat sensor system according to claim 9 wherein the RFID sensor is connected to the user interface by a wired electrical connection.

11. A sweat sensor system according to claim 9 wherein the RFID sensor is connected to the user interface by an RF connection.

12. A sweat sensor system according to claim 8 wherein the user interface is connected to the measuring apparatus by a wired electrical connection.

13. A sweat sensor system according to claim 8 wherein the measuring apparatus is connected to the user interface by an RF connection.

14. A sweat sensor system according to claim 8 wherein the user interface contains previous data of the subject and is operable to determine whether the subject has a normal or non-normal ionic concentration level of said at least one particular electrolyte and recommend to the subject any required action to be taken.

* * * * *